(12) United States Patent
Alikhani et al.

(10) Patent No.: US 10,952,798 B2
(45) Date of Patent: Mar. 23, 2021

(54) LOCATION TRACKING ON A SURFACE

(71) Applicants: Saeed Alikhani, Tehran (IR); Javad Hasani bidgoli, Tehran (IR); Mohammad Jalal Sadeghi, Tehran (IR); Alireza Ahmadian, Tehran (IR); Farzam Farahmand, Tehran (IR); Saeed Sarkar, Tehran (IR)

(72) Inventors: Saeed Alikhani, Tehran (IR); Javad Hasani bidgoli, Tehran (IR); Mohammad Jalal Sadeghi, Tehran (IR); Alireza Ahmadian, Tehran (IR); Farzam Farahmand, Tehran (IR); Saeed Sarkar, Tehran (IR)

(73) Assignee: PARSEH INTELLIGENT SURGICAL SYSTEM, Tehran (IR)

( * ) Notice: Subject to any disclaimer, the term of this patent is extended or adjusted under 35 U.S.C. 154(b) by 198 days.

(21) Appl. No.: 15/894,459

(22) Filed: Feb. 12, 2018

(65) Prior Publication Data
US 2018/0168739 A1 Jun. 21, 2018

Related U.S. Application Data

(60) Provisional application No. 62/457,905, filed on Feb. 12, 2017.

(51) Int. Cl.
| | |
|---|---|
| *A61B 34/20* | (2016.01) |
| *G01D 5/22* | (2006.01) |
| *G01B 7/00* | (2006.01) |
| *A61B 90/00* | (2016.01) |
| *A61B 17/00* | (2006.01) |

(52) U.S. Cl.
CPC .............. *A61B 34/20* (2016.02); *G01B 7/003* (2013.01); *G01D 5/2291* (2013.01); *A61B 2017/00119* (2013.01); *A61B 2034/2059* (2016.02); *A61B 2090/0811* (2016.02)

(58) Field of Classification Search
None
See application file for complete search history.

(56) References Cited

U.S. PATENT DOCUMENTS

| | | | |
|---|---|---|---|
| 4,750,489 A * | 6/1988 | Berkman | ................. A61F 9/013 351/205 |
| 7,262,614 B1 * | 8/2007 | Campbell | .......... G01R 1/06788 324/755.05 |
| 7,744,605 B2 | 6/2010 | Vilsmeier et al. | |
| 9,410,802 B2 | 8/2016 | Mucha et al. | |

(Continued)

FOREIGN PATENT DOCUMENTS

CN 104887327 A 3/2017

*Primary Examiner* — Paresh Patel
(74) *Attorney, Agent, or Firm* — Bajwa IP Law Firm; Haris Zaheer Bajwa (57) ABSTRACT

A location tracking apparatus and method of tracking are disclosed. The location tracking apparatus includes a tip configured to move on a surface, a tracking instrument, and a frictionless sensor associated with the tip. The tip is configured to undergo a displacement within a limited range when the tip is pushed to the surface, or when the tip is moved away from the surface, so that the tip maintains contact with the surface while moving on the surface. The tracking instrument is configured to generate location data. The frictionless sensor is configured to generate displacement data.

12 Claims, 5 Drawing Sheets

(56) References Cited

U.S. PATENT DOCUMENTS

| | | |
|---|---|---|
| 9,622,832 B2 | 4/2017 | Birkenbach et al. |
| 10,215,776 B2 * | 2/2019 | Campbell .......... G01R 1/06766 |
| 2003/0217478 A1 * | 11/2003 | Matsumiya ............ B82Y 30/00 |
| | | 33/784 |
| 2007/0299334 A1 | 12/2007 | Vilsmeier |
| 2010/0063387 A1 | 3/2010 | Timinger |
| 2014/0276007 A1 | 9/2014 | Sela et al. |
| 2016/0249986 A1 | 9/2016 | Krüger et al. |

* cited by examiner

LOCATION TRACKING ON A SURFACE

CROSS-REFERENCE TO RELATED APPLICATION

This application claims the benefit of priority from U.S. Provisional Patent Application Ser. No. 62/457,905, filed on Feb. 12, 2017, and entitled "ENHANCED SYSTEM FOR 3D SURFACE DATA ACQUISITION," which is incorporated herein by reference in its entirety.

SPONSORSHIP STATEMENT

This application has been sponsored by Iran Patent Center, which does not have any rights in this application.

TECHNICAL FIELD

The present disclosure generally relates to tracking instruments, and particularly, to an apparatus for location tracking on a surface.

BACKGROUND

In image-guided surgery systems, patient registration procedures are used at initial steps of the surgery for detecting both the location of a medical instrument as well as the position of a target under surgery. These procedures may be performed with a tracking instrument. During these types of procedures, the tracking instrument is configured to record location data of a medical instrument during surgery. The results are registered on images of the tissues under surgery. The tracking instrument may touch the tissue surface to record the location data and the reliability and precision of the recorded data may depend on the level of tissue surface deformation caused by the tracking instrument. However, the tissue surface deformation may invalidate the recorded data and the registration results.

There is, therefore, a need in the art for a location tracking instrument that is associated with minimal deformation on a target surface. There is also a need in the art for a location tracking instrument that maintains contact with a surface during a location tracking procedure without producing significant deformations on the surface.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a location tracking apparatus. The apparatus includes a tip configured to move and undergo displacement in at least a first dimension within a limited range, a tracking instrument configured to provide location data for the tip, as well as a frictionless sensor associated with the tip configured to generate displacement data for the tip. In some implementations, the frictionless sensor may be configured to generate the displacement data in real-time.

The above general aspect may include one or more of the following features. In one example, the apparatus also includes a primary shaft with a proximal end and a distal end, the distal end being connected to the tip, and a spring disposed adjacent to the primary shaft, where the spring is configured to help maintain contact between the tip and a surface while the tip is moving along the surface. In some implementations, the apparatus further includes a secondary shaft, where a distal end of the secondary shaft is connected to the frictionless sensor, and a proximal end of the secondary shaft is connected to the tracking instrument. In another example, the apparatus includes a linear variable differential transformer (LVDT) that includes a core, where the core is connected to a proximal end of the primary shaft, and the LVDT being included in the frictionless sensor. In some cases, a distal end of the secondary shaft is connected to the LVDT and a proximal end of the secondary shaft is connected to the tracking instrument. In another implementation, the frictionless sensor further includes a rotary variable differential transformer (RVDT). In one implementation, the apparatus further includes an electronic circuit configured to receive the location data from the tracking instrument and the displacement data from the frictionless sensor. In some cases, the electronic circuit is further configured to generate an alarm when the displacement data falls below a lower displacement threshold or exceeds a higher displacement threshold. In one example, the electronic circuit is also configured to transmit the location data and the displacement data to a processing unit, the processing unit being configured to generate position data including information regarding a position of the tip. In some cases, the processing unit is further configured to execute a process that includes: converting the displacement data to a transform vector, and converting the location data to a two-dimensional transform matrix. Furthermore, the process can include calculating a three-dimensional transform matrix by combining the transform vector and the two-dimensional transform matrix, and extracting the position of the tip from the three-dimensional transform matrix. In some implementations, the RVDT includes a rotor shaft connected to the proximal end of the primary shaft, the tip configured to rotate the rotor shaft through the primary shaft in a limited rotational range around an axis of the rotor shaft, the limited rotational range including a lower rotation limit and a higher rotation limit, the lower rotation limit corresponding to the lower displacement threshold and the higher rotation limit corresponding to the higher displacement threshold. In other implementations, the tip includes a lightweight tab that is configured to undergo an angular displacement in a limited angular displacement range when the tip is pushed toward the surface or when the tip is moved away from the surface in order to permit the tip to maintain contact with the surface, the limited angular displacement range including a lower angular displacement limit and a higher angular displacement limit, the lower angular displacement limit corresponding to the lower displacement threshold and the higher angular displacement limit corresponding to the higher displacement threshold. In another example, the tip is configured to push and pull the core through the primary shaft within a limited linear displacement range, the limited linear displacement range including a lower linear displacement limit and a higher linear displacement limit, the lower linear displacement limit corresponding to the lower displacement threshold and the higher linear displacement limit corresponding to the higher displacement threshold. In some cases, the limited range includes a zero-point, a lower limit, and a higher limit, the zero-point being located at a fixed distance from the tracking instrument.

In another general aspect, the present disclosure describes a method for location tracking using a location tracking apparatus. The method includes moving a tip of the location tracking apparatus along a surface while maintaining contact between the tip and the surface as the tip changes position relative to the surface by permitting displacement of the tip within a limited range as the tip is pushed toward the surface and away from the surface, the limited range including a zero-point, a lower limit, and a higher limit, the zero-point being located at a fixed distance from a tracking instrument of the location tracking apparatus. The method also includes generating location data for the tip by application of the tracking instrument, the location data including information of a location of the tip when the tip is placed at the zero-point. In addition, the method involves generating displacement data for the tip by application of a frictionless sensor associated with the tip, the displacement data including information regarding the displacement of the tip with respect to the zero-point. Furthermore, in some implementations, the method includes generating an alarm by application of an electronic circuit associated with the frictionless sensor, the alarm being triggered by a value of the displacement data being below a lower displacement threshold or above a higher displacement threshold, the lower displacement threshold corresponding to the lower limit, and the higher displacement threshold corresponding to the higher limit. In some implementations, the method also includes transmitting the location data and the displacement data to a processing unit when the value of the displacement data is between the lower displacement threshold and the higher displacement threshold, and generating position data for the tip based on at least the location data and the displacement data, the position data including information regarding a position of the tip.

The above general aspect may include one or more of the following features. In one example, the step of generating the displacement data by the frictionless sensor further includes rotating a rotor shaft of a rotary variable differential transformer (RVDT), the rotor shaft being connected to a primary shaft such that the rotor shaft can only rotate within a limited rotation range, the limited rotation range including a lower rotation limit and a higher rotation limit, the lower rotation limit corresponding to the lower displacement threshold and the higher rotation limit corresponding to the higher displacement threshold, as well as generating the displacement data by application of the RVDT. In another example, the step of moving the tip along the surface further includes angular displacement of a lightweight tab of the tip, the angular displacement being limited to a range extending between a lower angular displacement limit and a higher angular displacement limit, the lower angular displacement limit corresponding to the lower displacement threshold and the higher angular displacement limit corresponding to the higher displacement threshold. In some implementations, the method can also include pushing and pulling a core of a linear variable differential transformer (LVDT) within a limited linear displacement range, the limited linear displacement range including a lower linear displacement limit and a higher linear displacement limit, the lower linear displacement limit corresponding to the lower displacement threshold and the higher linear displacement limit corresponding to the higher displacement threshold, and generating the displacement data by use of the LVDT. In one implementation, the step of generating the displacement data by the frictionless sensor further includes: converting the displacement data to a transform vector, and converting the location data to a two-dimensional transform matrix. In some cases, the step of generating the displacement data by the frictionless sensor further includes: calculating a three-dimensional transform matrix by combining the transform vector and the two-dimensional transform matrix, and extracting the position data from the three-dimensional transform matrix.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary implementations of the present disclosure. For purposes of explanation, specific nomenclature is set forth to provide a thorough understanding of the present disclosure. However, it will be apparent to one skilled in the art that these specific details are not required to practice the disclosed exemplary implementations. Descriptions of specific exemplary implementations are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The present disclosure describes implementations of a method and an apparatus for tracking the location of a target under study. In some implementations, the apparatus may include a tip that moves on or along a surface of the target with little or no deformation of the surface. This may improve the accuracy of location tracking. In one implementation, the displacements of the tip may be measured by a frictionless sensor that can instantly sense small displacements without application of significant pressure to the tip. In some implementations, the frictionless sensor may be connected to a tracking instrument configured to record an initial location of the tip. In one implementation, the displacement data of the tip may be processed along with the initial location data to generate three-dimensional position data for the tip. In some implementations, the method may also include generating an alarm if the measured displacement data exceeds a valid displacement range.

Figure 1:
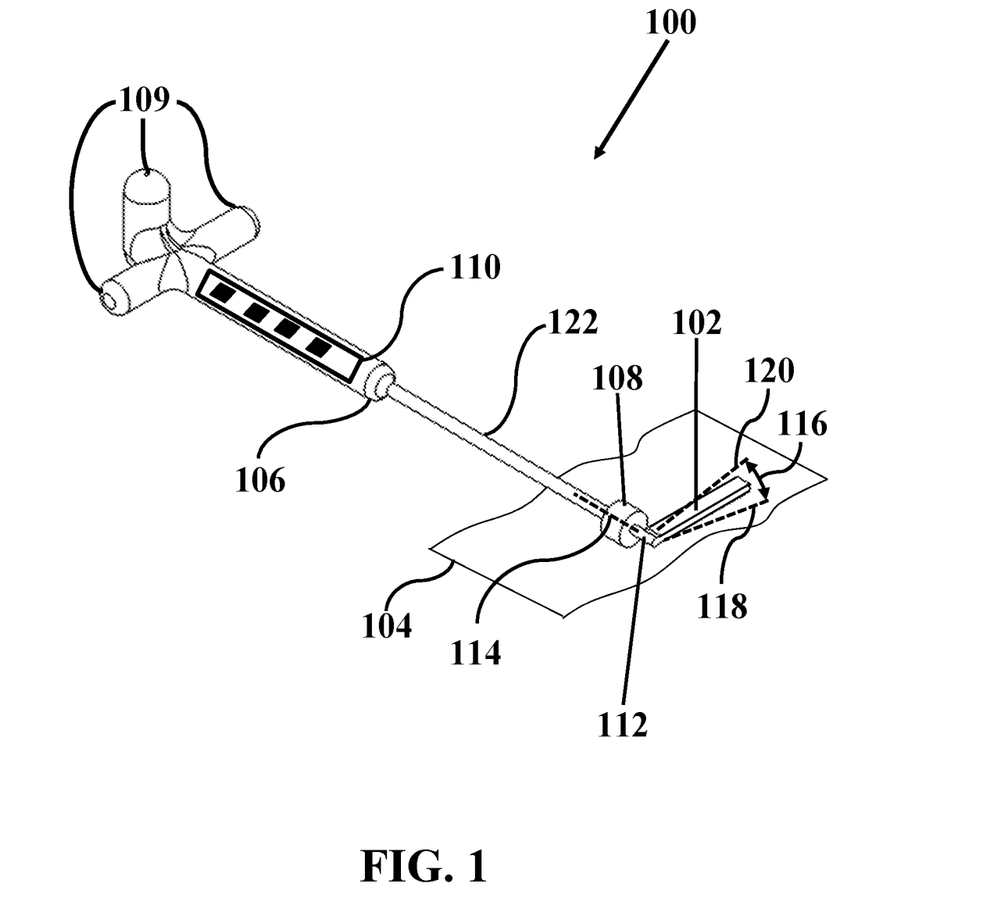
FIG. 1 is an illustration of an implementation of a location tracking apparatus.

Referring now to FIG. 1, a location tracking apparatus 100 is illustrated, according to one or more implementations of the present disclosure. As shown in the implementation of FIG. 1, the location tracking apparatus 100 includes a tip 102, a tracking instrument 106, and a frictionless sensor 108 associated with the tip 102. In some implementations, the tip 102 is configured move on or over a surface 104. As an example, the surface 104 may include a human skin surface or an animal skin surface. In some examples, the tip 102 may be configured to experience or undergo a displacement in a limited or otherwise restricted range when the tip 102 is pushed to or against the surface 104, and/or when the tip 102 is moved away from the surface 104. In some implementations, the tip 102 is configured to maintain contact with the surface 104 as the tip 102 moves relative to the surface 104.

Furthermore, in different implementations, the limited or restricted range may include a zero-point, a lower limit, and/or a higher limit. In some cases, the tracking instrument 106 may be configured to generate location data. As one example, the location data may include information regarding a location of the tip 102 when the tip 102 is placed at or approximately at the zero-point. In some implementations, the zero-point may be located at a fixed distance from the tracking instrument. Therefore, in some cases, the tracking instrument 106 may be configured to measure an initial location of the tip 102 for each point or a plurality of points on the surface 104. In some examples, a plurality of markers 109 may be placed on the tracking instrument 106 to generate three-dimensional coordinates for the location data. In one implementation, the coordinates can be generated to align with a Cartesian coordinate system such as $(x_0, y_0, z_0)$, though in other implementations any other location identification or coordinate system can be used.

In some implementations, the tracking instrument 106 may be coupled with a medical instrument to track the location of the medical instrument while the medical instrument is moving on or along the surface 104. In some cases, the frictionless sensor 108 may be configured to sense displacements of the tip 102. Furthermore, in one implementation, the frictionless sensor 108 may be configured to generate displacement data of the tip 102 in real-time. The displacement data may include information regarding the displacement of the tip 102 with respect to the zero-point. As an example, if the zero-point is located at $(x_0, y_0, z_0)$, and the surface 104 has irregularities in the z-direction, the tip 102 may be displaced in the z-direction when reaching the point $(x_0, y_0, z_0)$ while moving on the surface 104. Hence, the displacement data may include a $\Delta z$ displacement. Because the tip 102 is also configured to maintain contact with the surface 104, the tip 102 may be moved proximally toward or pushed against the surface 104 when approaching or coming upon an irregularity on the surface 104 in some cases. In other cases, the tip 102 can be moved distally away from the surface 104 when approaching or coming upon an irregularity on the surface 104. This shift in position may cause or be associated with an application of a slight force to the frictionless sensor 108. The frictionless sensor 108 may, among other information, convert this force into displacement data. Thus, irregularities of the surface 104 may be sensed and measured without significant deformation on the surface 104.

In different implementations, the frictionless sensor 108 may be further associated with an electronic circuit 110. In some implementations, the electronic circuit 110 may be disposed within or otherwise connected to the tracking instrument 106. In one implementation, the electronic circuit 110 may be configured to receive displacement data from the frictionless sensor 108. In addition, in some implementations, the electronic circuit 110 can be configured to generate an alarm responsive to the displacement data indicating specific events. For example, an alarm may be generated if the displacement data is at or below a lower displacement threshold or at or above a higher displacement threshold. In such cases, the lower displacement threshold may correspond to the lower limit, and the higher displacement threshold may correspond to the higher limit. The alarm may serve as a warning or alert to an operator of the location tracking apparatus 100. For example, an operator may modify the placement of the location tracking apparatus 100 in response to the alarm in order to ensure the collection of valid displacement data.

In different implementations, the frictionless sensor 108 may further include a rotary variable differential transformer (RVDT). The RVDT may be used to measure angular displacements. In some implementations, the RVDT may include a rotor shaft (obscured from view in FIG. 1). The rotor shaft may be connected to a proximal end of a primary shaft 112. Furthermore, a distal end of the primary shaft 112 may be connected to the tip 102. In one implementation, the tip 102 may be configured to facilitate rotation of the rotor shaft through the primary shaft 112 in a limited rotational range around an axis 114 of the rotor shaft. In some implementations, the limited rotational range may include a lower rotation limit and a higher rotation limit. The lower rotation limit may correspond to the lower displacement threshold, and the higher rotation limit may correspond to the higher displacement threshold.

In some implementations, the tip 102 further includes include a lightweight tab. The lightweight tab may be configured to experience or undergo an angular displacement within a limited angular displacement range 116 when the tip 102 is pushed to the surface 104, or when the tip 102 is moved away from the surface 104, such that the tip 102 maintains contact with the surface 104 while moving along the surface 104. The limited angular displacement range 116 may include a lower angular displacement limit 118 and a higher angular displacement limit 120. The lower angular displacement limit 118 may correspond to the lower displacement threshold and the higher angular displacement limit 120 may correspond to the higher displacement threshold. Since the lightweight tab may be configured to maintain continuous or substantially continuous contact with the surface 104, the tab may be pushed to the surface 104 or moved away from the surface 104 when the tip 102 reaches an irregularity on the surface 104. This may lead to the angular displacement of the lightweight tab in the limited angular displacement range 116. The angular displacement of the lightweight tab may cause or be associated with a rotation of the primary shaft 112, as well as a rotation of the rotary shaft of the RVDT around the axis 114. In some implementations, the RVDT may then convert the rotation of the rotary shaft to the displacement data.

As shown in FIG. 1, in some implementations, the location tracking apparatus 100 may further include a secondary shaft 122. A distal end of the secondary shaft 122 may be connected to the frictionless sensor 108, and a proximal end of the secondary shaft 122 may be connected to the tracking instrument 106.

Figure 2:
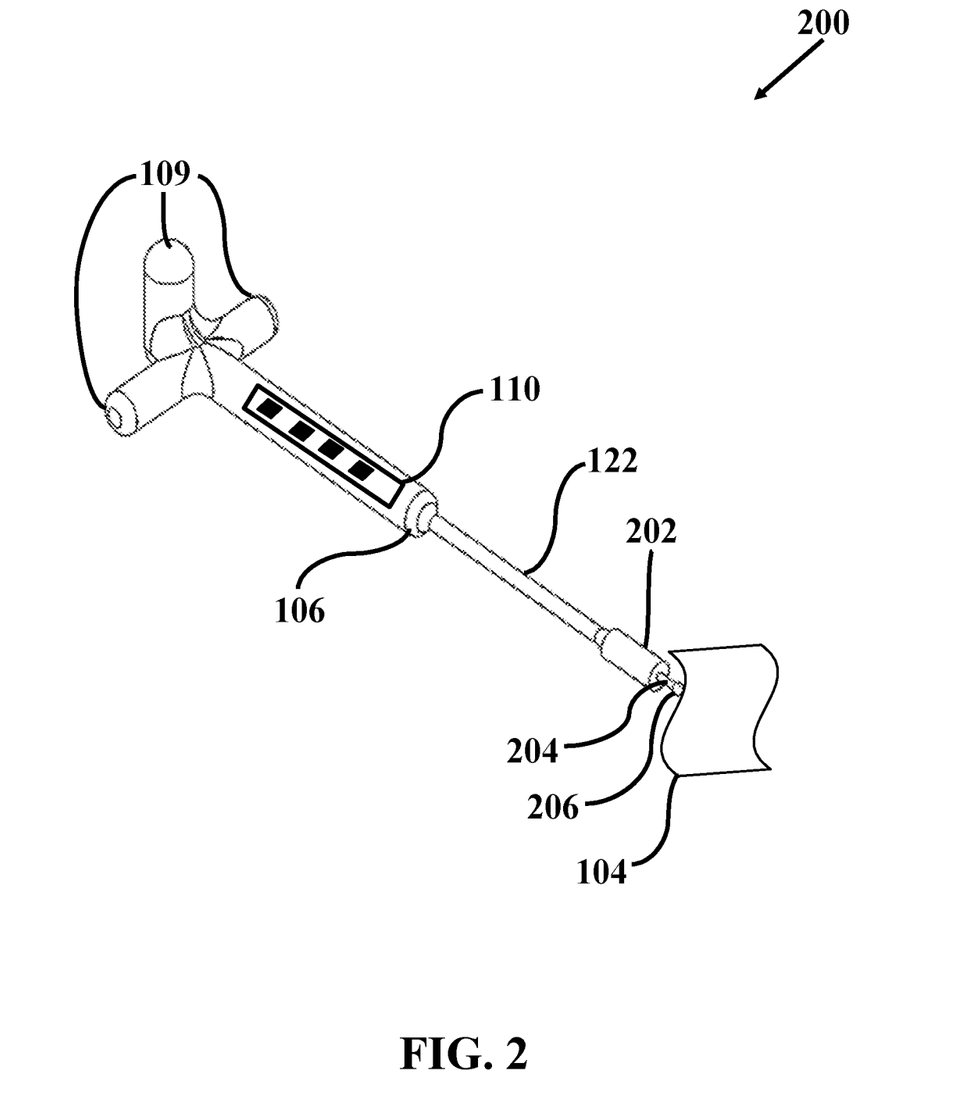
FIG. 2 is an illustration of an implementation of a location tracking apparatus.

Referring now to FIG. 2, an implementation of a location tracking apparatus 200 is depicted. As shown in FIG. 2, in some implementations, the frictionless sensor 108 may include a linear variable differential transformer (LVDT) 202. The LVDT 202 may be configured to measure linear displacements. In some implementations, the LVDT 202 may include a core (obscured from view in FIG. 2) that is connected to a proximal end of a primary shaft 204. A distal end of the primary shaft 204 may be connected to a tip 206.

Figure 3:
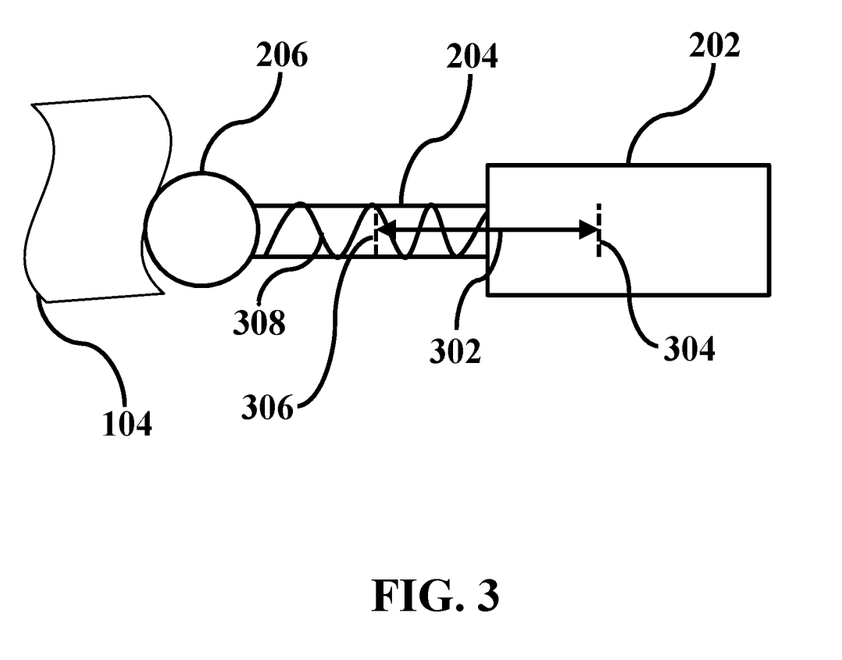
FIG. 3 is an illustration of an implementation of a primary shaft of a location tracking apparatus.

Referring next to FIG. 3, in some examples, it should be understood that the tip 206 may be configured to push and pull the core through the primary shaft 204 within a limited linear displacement range 302. The limited linear displacement range 302 may include a lower linear displacement limit 304 and a higher linear displacement limit 306. In some implementations, the lower linear displacement limit 304 may correspond to the lower displacement threshold and the higher linear displacement limit 306 may correspond to the higher displacement threshold.

In some implementations, the location tracking apparatus 200 may further include a spring 308, as shown in FIG. 3. The spring 308 may be disposed substantially around, encircle, surround or be otherwise disposed adjacent to the primary shaft 204. In one implementation, the spring 308 is configured to maintain contact between the tip 206 and the surface 104 while the tip 206 is moving along the surface 104. When the tip 206 reaches or comes upon an irregularity on the surface 104, the tip 206 may be pushed toward the surface 104 or moved away from the surface 104. Furthermore, the tip 206 may consequently push or pull the primary shaft 204, leading to a linear displacement of the primary shaft 204, as well as the core of the LVDT 202, in the limited linear displacement range 302. The LVDT 202 may then convert the linear displacement of the core to the displacement data in some implementations.

Figure 4:
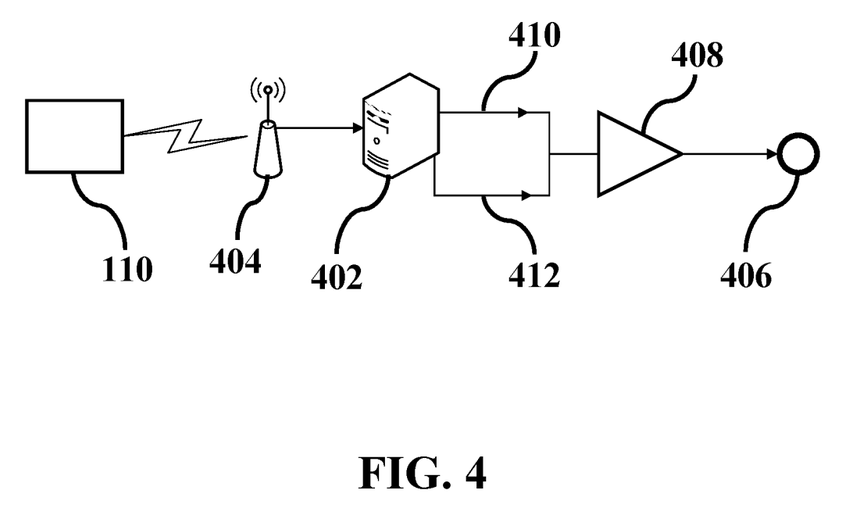
FIG. 4 is a block diagram representing an implementation of a transmitting and processing mechanism.

Referring now to the block diagram of FIG. 4, in different implementations, the electronic circuit 110 may be further configured to receive the location data from the tracking instrument 106. Furthermore, in some implementations, the electronic circuit 110 can be configured to transfer the location data and the displacement data to a processing unit 402, responsive to the displacement data remaining between the lower displacement threshold and the higher displacement threshold. In some cases, the electronic circuit 110 may then transfer or transmit the location data and the displacement data via a transmitting device 404. In some implementations, the transmitting device 404 may include a wireless module or a cabled connection. In one example, the wireless module may be embedded inside or otherwise connected to the tracking instrument 106. In one implementation, the processing unit 402 may be configured to generate position data 406 by performing or executing a process 408 on the location data 410 and the displacement data 412. The position data 406 may include information about a position of the tip 102 in some implementations.

Figure 5:
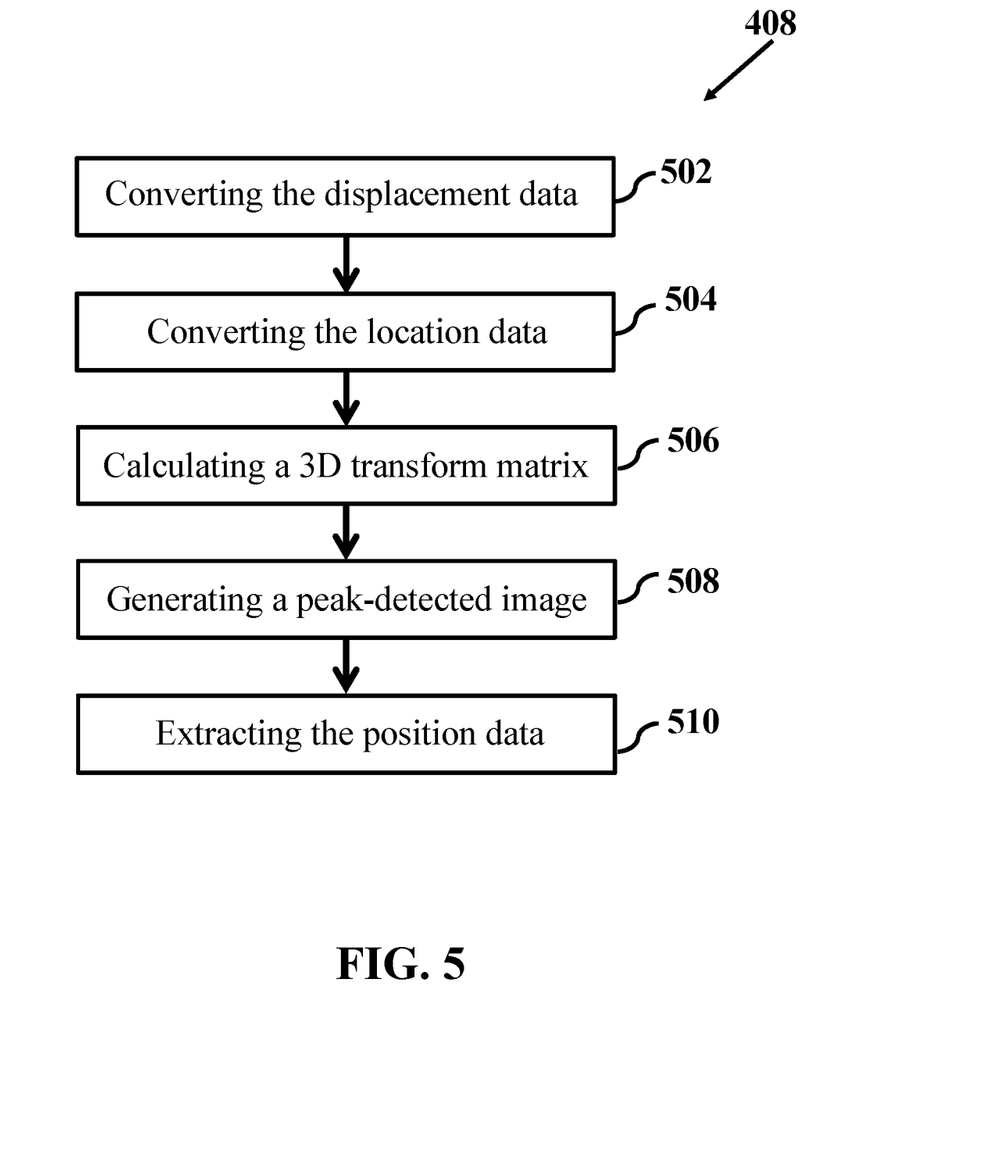
FIG. 5 is a flowchart depicting an implementation of a process for generation of position data by a processing unit.

For purposes of clarity to the reader, one implementation of the process 408 is presented in the flowchart of FIG. 5. In some implementations, the process 408 may include a first step 502 of converting the displacement data 412 to a transform vector, and a second step 504 of converting the location data 410 to a two-dimensional transform matrix. In addition, in some implementations, the process 408 includes a third step 506 of calculating a three-dimensional transform matrix by combining the transform vector and the two-dimensional transform matrix. In some implementations, an optional fourth step 508 includes generation of a peak-detected image. The process 408 further includes a fifth step 510 of extracting the position data 406 from the three-dimensional transform matrix. In different implementations, the position data 406 may include the information of an immediate position of the tip 102, for example $(x_1, y_1, z_1)$, which is resulted from the displacement of the tip 102 from the zero-point $(x_0, y_0, z_0)$.

Thus, in different implementations, the implementations described herein can provide a method for location tracking. In some implementations, the method can initially involve moving a tip of the location tracking apparatus along a surface while maintaining contact between the tip and the surface as the tip changes position relative to the surface. In one implementation, the contact can be maintained at least in part by permitting displacement of the tip within a limited range as the tip is pushed toward the surface and away from the surface. Furthermore, the limited range may be understood to include a zero-point, a lower limit, and a higher limit, where the zero-point is located at a fixed distance from a tracking instrument of the location tracking apparatus. In addition, in some implementations, the method can include generating location data for the tip by application of the tracking instrument. For example, the location data can provide information of a location of the tip when the tip is placed at the zero-point or other position data. In some implementations, the method also includes generating displacement data for the tip by application of a frictionless sensor associated with the tip, where the displacement data includes information regarding the displacement of the tip with respect to the zero-point. In another implementation, the method includes generating an alarm by application of an electronic circuit associated with the frictionless sensor. For example, the alarm may be triggered by a value of the displacement data being below a lower displacement threshold or above a higher displacement threshold. In such cases, the lower displacement threshold corresponding to the lower limit, and the higher displacement threshold corresponding to the higher limit. In some implementations, the method can further include transmitting the location data and the displacement data to a processing unit when the value of the displacement data is between the lower displacement threshold and the higher displacement threshold. In one implementation, the method can also include generating position data for the tip. This data can be generated based on at least the location data and/or the displacement data, and in some cases the position data includes information regarding a position of the tip.

In other implementations, the location tracking method can include additional or different, optional steps. For example, the step of generating the displacement data by the frictionless sensor may further include rotating a rotor shaft of a rotary variable differential transformer (RVDT). In one implementation, the rotor shaft can be connected to a primary shaft such that the rotor shaft can only rotate within a limited rotation range. The limited rotation range may include a lower rotation limit and a higher rotation limit, where the lower rotation limit corresponds to the lower displacement threshold and the higher rotation limit corresponds to the higher displacement threshold. In some implementations, the method may include generating the displacement data by application of the RVDT.

In some other implementations, moving the tip along the surface further includes angular displacement of a light-weight tab of the tip. In one implementation, the angular displacement is limited to a range extending between a lower angular displacement limit and a higher angular displacement limit, where the lower angular displacement limit corresponds to the lower displacement threshold and the higher angular displacement limit corresponds to the higher displacement threshold.

In different implementations, the method may further involve pushing and/or pulling a core of a linear variable differential transformer (LVDT) within a limited linear displacement range. In such cases, the limited linear displacement range may include a lower linear displacement limit and a higher linear displacement limit, where the lower linear displacement limit corresponds to the lower displacement threshold and the higher linear displacement limit corresponds to the higher displacement threshold. In one implementation, the method can include generating the displacement data by use of the LVDT.

In other implementations, the step of generating the displacement data by the frictionless sensor further includes: converting the displacement data to a transform vector, converting the location data to a two-dimensional transform matrix, calculating a three-dimensional transform matrix by combining the transform vector and the two-dimensional transform matrix, and/or extracting the position data from the three-dimensional transform matrix While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A location tracking apparatus comprising:
   a primary shaft with a proximal end and a distal end;
   a tip movably connected to the distal end of the primary shaft, the tip configured to undergo displacement with respect to an initial location of the tip in at least a first dimension within a limited range responsive to the tip being pushed to a surface of an object or the tip being moved away from the surface;
   a tracking instrument configured to provide location data by measuring the initial location while being moved along the surface of the object by an operator, the initial location comprising a zero-point located at a fixed distance from the tracking instrument;
   a frictionless sensor connected to the proximal end of the primary shaft, the frictionless sensor configured to generate displacement data by measuring the displacement of the tip;
   a secondary shaft with a proximal end and a distal end, the proximal end of the secondary shaft connected to the tracking instrument and the distal end of the secondary shaft connected to the frictionless sensor;
   an electronic circuit disposed within the tracking instrument, the electronic circuit configured to:
      receive the location data from the tracking instrument;

receive the displacement data from the frictionless sensor; and transmit the location data and the displacement data to a processing unit, the processing unit configured to generate position data comprising information regarding a position of the tip by combining the location data and the displacement data.

2. The location tracking apparatus of claim 1, further comprising a spring disposed adjacent to the primary shaft, the spring configured to help maintain contact between the tip and the surface while the tip is moving along the surface by pushing the tip toward the zero-point responsive to the tip being displaced from the zero-point.

3. The location tracking apparatus of claim 2, further comprising
a linear variable differential transformer (LVDT) including a core connected to the proximal end of the primary shaft, the LVDT being included in the frictionless sensor, wherein the distal end of the secondary shaft is connected to the LVDT.

4. The location tracking apparatus of claim 1, wherein the frictionless sensor comprises a rotary variable differential transformer (RVDT).

5. The location tracking apparatus of claim 1, wherein the electronic circuit is further configured to generate an alarm when the displacement data falls below a lower displacement threshold or exceeds a higher displacement threshold.

6. The location tracking apparatus of claim 1, wherein the processing unit is further configured to execute a process that includes:
converting the displacement data to a transform vector; and
converting the location data to a two-dimensional transform matrix.

7. The location tracking apparatus of claim 6, wherein the process further includes:
calculating a three-dimensional transform matrix by combining the transform vector and the two-dimensional transform matrix; and
extracting the position of the tip from the three-dimensional transform matrix.

8. The location tracking apparatus of claim 4, wherein the RVDT includes a rotor shaft connected to the proximal end of the primary shaft, the tip configured to rotate the rotor shaft through the primary shaft in a limited rotational range around an axis of the rotor shaft, the limited rotational range comprising a lower rotation limit and a higher rotation limit, the lower rotation limit corresponding to the lower displacement threshold and the higher rotation limit corresponding to the higher displacement threshold.

9. The location tracking apparatus of claim 8, wherein the tip comprises a lightweight tab configured to undergo an angular displacement around the axis of the rotor shaft in a limited angular displacement range when the tip is pushed toward the surface or when the tip is moved away from the surface in order to permit the tip to maintain contact with the surface, the limited angular displacement range comprising a lower angular displacement limit and a higher angular displacement limit, the lower angular displacement limit corresponding to the lower displacement threshold and the higher angular displacement limit corresponding to the higher displacement threshold.

10. The location tracking apparatus of claim 3, wherein the tip is configured to push and pull the core through the primary shaft within a limited linear displacement range, the limited linear displacement range including a lower linear displacement limit and a higher linear displacement limit, the lower linear displacement limit corresponding to the lower displacement threshold and the higher linear displacement limit corresponding to the higher displacement threshold.

11. The location tracking apparatus of claim 1, wherein the limited range comprises zero displacement corresponding to the zero-point, a lower limit, and a higher limit.

12. A location tracking apparatus comprising:
a primary shaft with a proximal end and a distal end;
a tip movably connected to the distal end of the primary shaft, the tip comprising a lightweight tab configured to undergo angular displacement around the primary shaft with respect to an initial location of the tip within a limited range responsive to the tip being pushed to a surface of an object or the tip being moved away from the surface;
a tracking instrument configured to provide location data by measuring the initial location of the tip while being moved along the surface of the object by an operator, the initial location comprising a zero-point located at a fixed distance from the tracking instrument;
a rotary variable differential transformer (RVDT) connected to the proximal end of the primary shaft, the RVDT configured to generate displacement data by measuring the angular displacement of the tip;
a secondary shaft with a proximal end and a distal end, the proximal end of the secondary shaft connected to the tracking instrument and the distal end of the secondary shaft connected to the RVDT;
an electronic circuit disposed within the tracking instrument, the electronic circuit configured to:
receive the location data from the tracking instrument;
receive the displacement data from the RVDT;
generate an alarm when the displacement data falls below a lower displacement threshold or exceeds a higher displacement threshold, the lower displacement threshold corresponding to the lower angular displacement limit and the higher displacement threshold corresponding to the higher angular displacement limit; and
transmit the location data and the displacement data to a processing unit, the processing unit configured to generate position data comprising information regarding a position of the tip by executing a process, the process comprising:
converting the displacement data to a transform vector;
converting the location data to a two-dimensional transform matrix;
calculating a three-dimensional transform matrix by combining the transform vector and the two-dimensional transform matrix; and
extracting the position data from the three-dimensional transform matrix;
wherein the limited range comprises zero displacement corresponding to the zero-point, a lower angular displacement limit, and a higher angular displacement limit.

* * * * *